US00PP09646P

United States Patent [19]

Ackerman

[11] Patent Number: Plant 9,646

[45] Date of Patent: Sep. 24, 1996

[54] RASPBERRY (RUBUS) VARIETY NAMED 'PSI-1014'

[75] Inventor: Stephen M. Ackerman, Salinas, Calif.

[73] Assignees: Plant Sciences, Inc.; Berry R & D, Inc., both of Watsonville, Calif.

[21] Appl. No.: 498,403

[22] Filed: Jul. 5, 1995

[51] Int. Cl.[6] ..... A01H 5/00

[52] U.S. Cl. ..... Plt./46.2

[58] Field of Search ..... Plt./46.2

*Primary Examiner*—James R. Feyrer

*Attorney, Agent, or Firm*—Christie, Parker & Hale, LLP

[57] ABSTRACT

Described is a new everbearing raspberry variety which is capable of producing fruit on first year primocanes, and both floricanes and primocanes in subsequent years.

5 Drawing Sheets

BACKGROUND OF THE INVENTION

This invention relates to a new and distinct everbearing red raspberry variety named 'PSI-1014' which is capable of producing fruit on first year primocanes, and both floricanes and primocanes in subsequent years.

The new variety of raspberry resulted from a breeding program with the objective of developing new and distinct raspberry varieties. The selection was made in a controlled breeding plot in Watsonville, Calif. After its selection in 1990, the new variety was further asexually propagated by dormant canes and roots and non-dormant root shoot cuttings, and extensively tested over the next several years. This propagation and asexual reproduction has demonstrated that the combination of traits disclosed herein as characterizing the new variety is fixed and remains true to type through successive generations of asexual reproduction.

SUMMARY OF THE INVENTION

The present invention relates to a new and distinct everbearing red raspberry variety designated as 'PSI-1014'. The new variety originated from a cross of 'Watson' (U.S. Pat. No. P.P. 7,076) and 'Summit'. The new variety is particularly characterized by early fall primocane production, beginning as early as July 1, with up to two-thirds of its total primocane production harvested by August 30, on the Central Coast of California. The new variety has also demonstrated its adaptation to the growing systems and styles of the San Diego, Calif. district. The fruit is dark with drouplets of uniform size and distribution. The fruit has a tendency to develop a slight waxy halo and does not separate easily from the receptacle, making it difficult to pick.

The following combination of characteristics is particularly distinguishing in 'PSI-1014':

1. Everbearing fruiting habit, fruits on first year primocanes;

2. Early fall fruiting habit from first year primocanes, as early as July 1 on the Central Coast of California;

3. Produces up to two-thirds of its total primocane yield by August 30;

4. Relatively tall plant; and

5. Dark uniform fruit with a tendency to develop a slight waxy halo.

'PSI-1014' may be distinguished from its parents by the following combination of characteristics:

Comparison With Other Varieties

Compared to 'Summit' the new variety is taller and more vigorous in growth. The foliage is larger, less corrugated and slightly more cupped. The new variety produces primarily three leaflets per leaf as compared to five for 'Summit'. The fruit of the new variety is more uniform in shape and drouplet distribution. Overall fall/spring production is greater than 'Summit', peaking as much as 1–2 weeks earlier in the fall and as much as 1–2 weeks earlier in the spring. Basal thorn color of the new variety is similar to the cane with a reddish purple tip, whereas 'Summit' is a purplish color from base to tip.

Compared to 'Watson' the fruit of the new variety is smaller, lighter in color, less glossy, more uniform in shape and drouplet distribution and of better quality. The primocane has fewer thorns, and the foliage is less twisted. Overall fall/spring production is greater than 'Watson'. Fall production begins as much as 3–4 weeks earlier and peaks as much as 6–8 weeks earlier than 'Watson'. Spring production also begins as much as 2–3 weeks earlier and peaks as much as 1–2 weeks earlier than 'Watson'.

BRIEF DESCRIPTION OF PHOTOGRAPHS AND FIGURES

The accompaning photographs show typical specimens of the new variety at various stages of development as true as it is possible to make in illustrations of this characer. Phenotypic expression may vary according to light, environmenal and cultural conditioning:

The accompaning photographs and drawing show:

typical fruiting terminal and developmental stages from flower to mature fruit;

typical mature leaf and leaflets depicting a raised midvein, and typical venation;

typical plant growth habits and fruiting characteristics; and typical fruit.

The drawing depicts the isozyme banding patterns for 'PSI-1014', 'Summit' and 'Watson' raspberries.

DESCRIPTION OF THE NEW VARIETY

The following is a detailed description of 'PSI-1014', including fruit production, together with the variety's morphological, electrophoretic, pest and disease reaction characteristics. The variety's characteristics are compared to those of its parents.

This detailed description of 'PSI-1014' is based on observations taken during the spring and summer of 1994 from plants planted as dormant root stock in early January of the same year in Watsonville, Calif. The characteristics of the new variety may vary slightly in detail, depending upon variations in environmental factors, including weather (temperature, humidity and light intensity), day length, soil type and location. 'PSI-1014' has not been observed under all possible environmental conditions. It has also not been tested for winter hardiness. Color terminology follows the Munsell Book of Colors, Munsell Color, Baltimore, Md. (1976).

Fruit and Fruit Production Characteristics

The new variety is primarily adapted to the climate and growing conditions of the Central California coast, where it was selected and tested. This region, near the Pacific Ocean, provides appropriate year-round temperatures to produce a strong vigorous plant, and to remain in fruit production for July through December and, in the ensuing year, from May through July. The new variety has also demonstrated its adaptation to the growing systems and styles of the San Diego, Calif. district, i.e., the planting of dormant canes and roots in midsummer for fall and winter (i.e., October-March) fruit production. The fruit of 'PSI-1014' is primarily suited to the fresh fruit market.

Initial yield studies show that 'PSI-1014' produces heavy primocane yields, greater than both 'Watson' and 'Summit' during the fall months, with overall yields from both primocanes and floricanes of 'PSI-1014' exceeding both 'Watson' and 'Summit'. Overall fruit size is comparable to 'Summit' but less than 'Watson'.

The new variety begins to fruit from first year primocanaes in early July, similar to 'Summit' but up to 4 weeks earlier than 'Watson', peaking in early August. Fruiting begins again on the floricanes in early May, 1–2 weeks earlier than both 'Watson' and 'Summit', peaking in early June.

The fresh fruit of 'PSI-1014' is medium-deep red in color at maturity, color near 2.5R 3/6. After 5 days of cold storage (1.1 degrees centigrade), the fruit darkens to a deep red color, color near 2.5R 2/6. The fruit is non-glossy with a tendency to develop a slight waxy halo over its exposed upper surface. The mature fruit is moderately firm and strongly attached to the receptacle The fruit possesses acceptable flavor and shipping quality. The fruit appearance may be slightly compromised due to the waxy halo.

The primary primocane fruit is conic in shape tapering to a blunt tip. The fruit averages from about 2.4 to 2.6 cm in axil length and 2.0 to 2.2 cm in axil diameter with an average length/width ratio of about 1.19 and an average weight of about 4.5 to 5.0 grams. Seeds from the primary fruit average from about 1.4 to 1.5 mgs in weight after drying for 48 hours at room temperature. The average primocane fruit harvested from July through November weighs from about 2.6 to 2.8 gms with an average of 70 to 80 medium to small uniformly shaped drouplets. The drouplets are evenly distributed around the berry and typically held even to the surface giving the berry a smooth textured surface. The season average primocane fruit tends to be more rounded than the primary fruit with a length/width ratio of 0.93. The average floricane berry harvested from May through July weighs from about 2.1 to 2.3 gms.

Plant Characteristics

The primocanes of 'PSI-1014' are vigorous, of erect habit, and with moderately dense foliage, averaging 1.8 m to 2.1 m in height. The plant tends to droop slightly under heavy fruit loads during peak production. The plant crown produces 2 to 6 primocanes per crown during the growing season and fruits on about one-third of the cane. The primocanes average from about 15 to 20 mm in diameter at the base and about 9 to 13 mm in diameter at approximately mid cane. Internodes are of medium length averaging from 5 to 7 cm in length.

The primocane is a light greenish yellow color, color near 2.5GY 7/4. Exposed canes tend to have a moderate reddish purple anthocyanin coloration, color near 2.5RP 4/4. The plant produces many lateral branches on the upper third of the cane. These laterals average from 22 to 33 cm in length and are semi-erect. Thorns are few yet stout averaging from 0.5 to 1.0 thorns per cm of cane and from 2.0 to 2.6 mm in length. The thorn tips are held horizontally relative to the cane axis. The basal thorn color is similar to the cane, color near 2.5GY 7/4 with a medium reddish purple tip, color near 7.5RP 3/6.

Floricanes are medium brown in color, color near 7.5YR 4/6 with a moderate number of lateral branches averaging from 10 to 20 per cane with an average length of 50 to 80 cm.

Foliage Characteristics

Mature leaves are medium green yellow, color near 7.5GY 3/4 on the upper surface and pale green yellow, color near 5GY 6/2 on the underside. Leaves are compound with primarily 3 leaflets per leaf with occasionally a 5-leaflet leaf. The terminal leaflets are cordate in shape tapering to an acuminae tip. Lateral leaflets are opposite. Leaf margins are serrated. The upper surface of the leaf is non-glossy. Leaves veins are moderate with an occasionally raised mid vein.

The terminal leaflet of a 3-leaflet leaf averages 14 to 16 cm in length and 9 to 12 cm in width with an average length/width ratio of 1.4 to 1.5. The lateral leaflet averages 11 to 13 cm in length and 6 to 8 cm in width with an average length/width ratio of 1.6 to 1.7. The rachis length between a pair of lateral leaflets and the terminal leaflet averages 3 to 4 mm in length. Petioles are light greenish yellow, color near 2.5GY 7/4, moderately thorned with 15 to 20 thorns per petiole and an average length of 6 to 8 cm.

Flowers

Flowers are medium in size, self-fertile and have 5 to 6 petals per flower. Each flower produces ample pollen for good pollination. Flowers and fruit are well exposed for easy access to picking.

Pest and Disease Reactions

It is not known whether the new variety is resistant to any of the known insects and diseases common in California. However, the new variety has been shown to be moderately susceptible to late yellow rust, and only slightly susceptible to cane borytis, fruit rot, and powdery mildew. It has not been tested for resistance to any of the root rot or virus complexes.

Isozymes in Leaf Extract

Studies of protein polymorphism in Rubus by the starch gel electrophoresis method were carried out to characterize this newly developed variety and distinguish it from similar appearing varieties.

Isozymes were extracted from young leaves and characterized, using starch gel electrophoresis techniques. The following isozymes were characterized: phosphoglucoisomerase (PGI: EC 5.3.1.9), phosphoglucomutase (PGM: EC 2.7.5.1) and triose phosphate isomerase (TPI: EC 5.3.1.1).

The testing used both field and greenhouse grown plant material, all grown in Watsonville, Calif. Newly mature leaves (0.5 g fresh weight) from the growing tips of the canes were used. Samples were collected in the morning, held at 4C and analyzed within six hours.

The tissue preparation, extraction and staining are as reported in S. Arulsekaar and D. E. Parfitt, "Isozyme Analysis Procedures for Stone Fruits, Almond, Grape, Walnut, Pistachio, and Fig." *HortScience* 21(4): 928–933.

Following electrophoresis, the gel was sliced and stained for each enzyme system. Banding patterns were interpreted as they developed, and gel slices were fixed in 50% glycerol.

The isozyme banding patterns of 'PSI-1014', compared to 'Summit' and 'Ruby', are given in the drawing. The pattern and band densities for PGM are distinctly different between 'PSI-1014' and 'Ruby' and the pattern and band densities for TPI are distinctly different between 'PSI-1014' and 'Summit'. The combination of isozyme patterns shown, derived from the specific techniques described, identify 'PSI-1014' with certainty as a unique raspberry variety.

What is claimed is:

1. A new and distinct red raspberry varietey named 'PSI-1014' as herein described and illustrated.

* * * * *

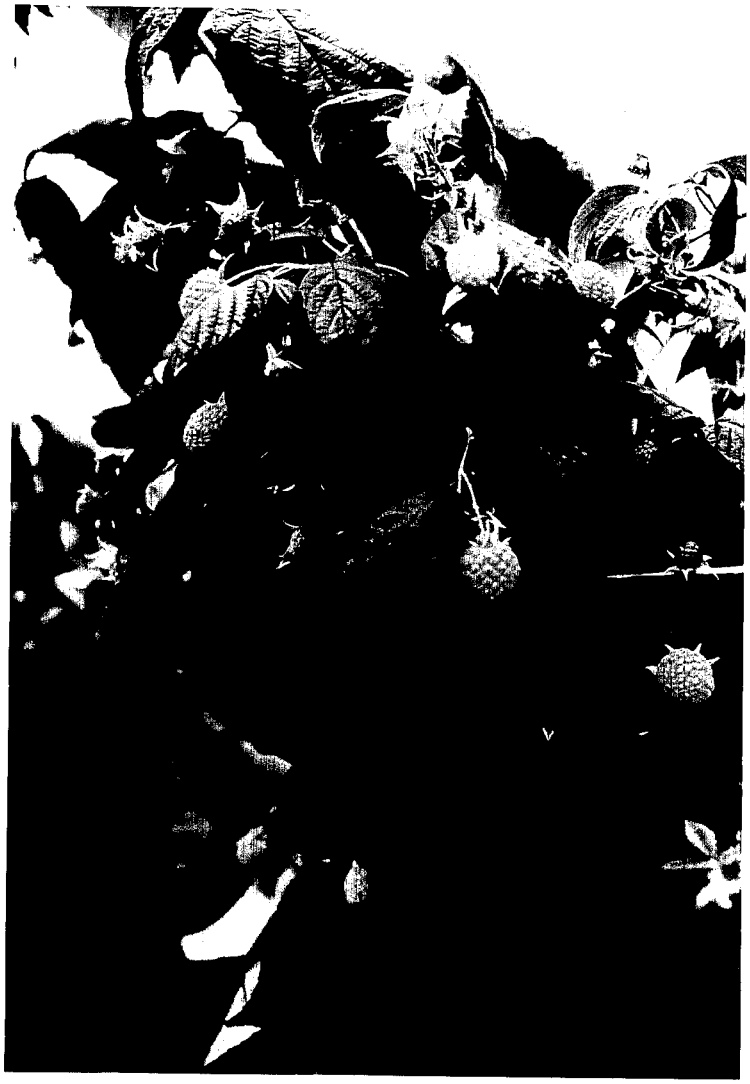

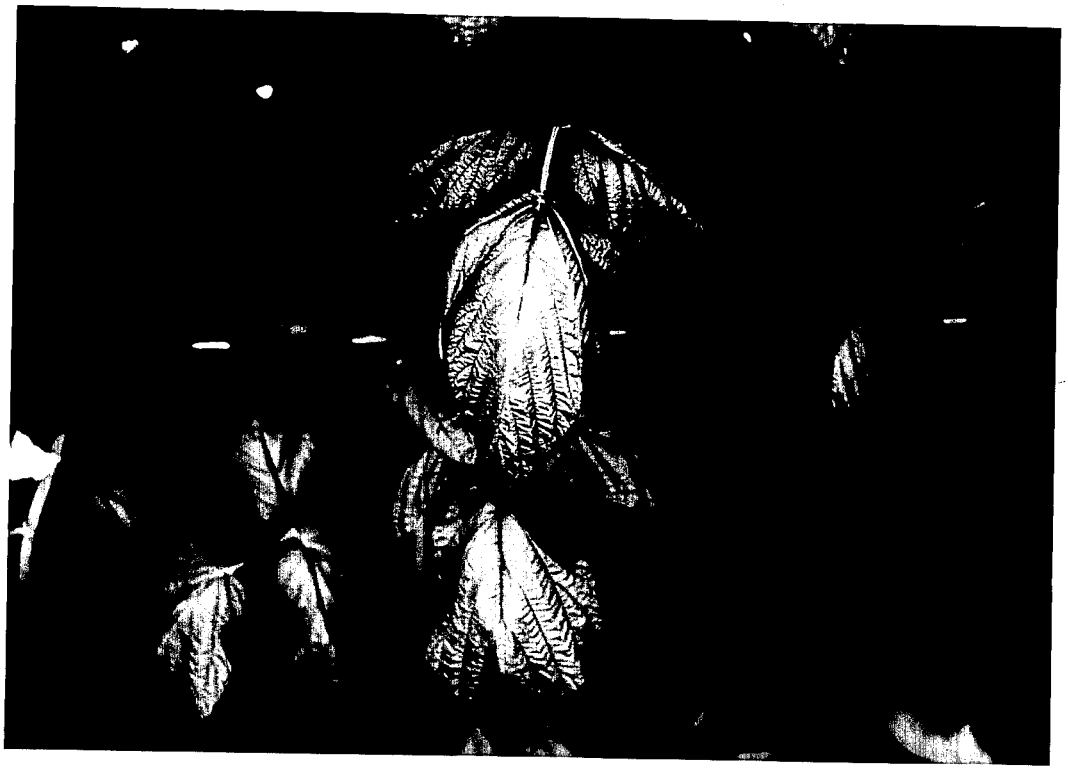

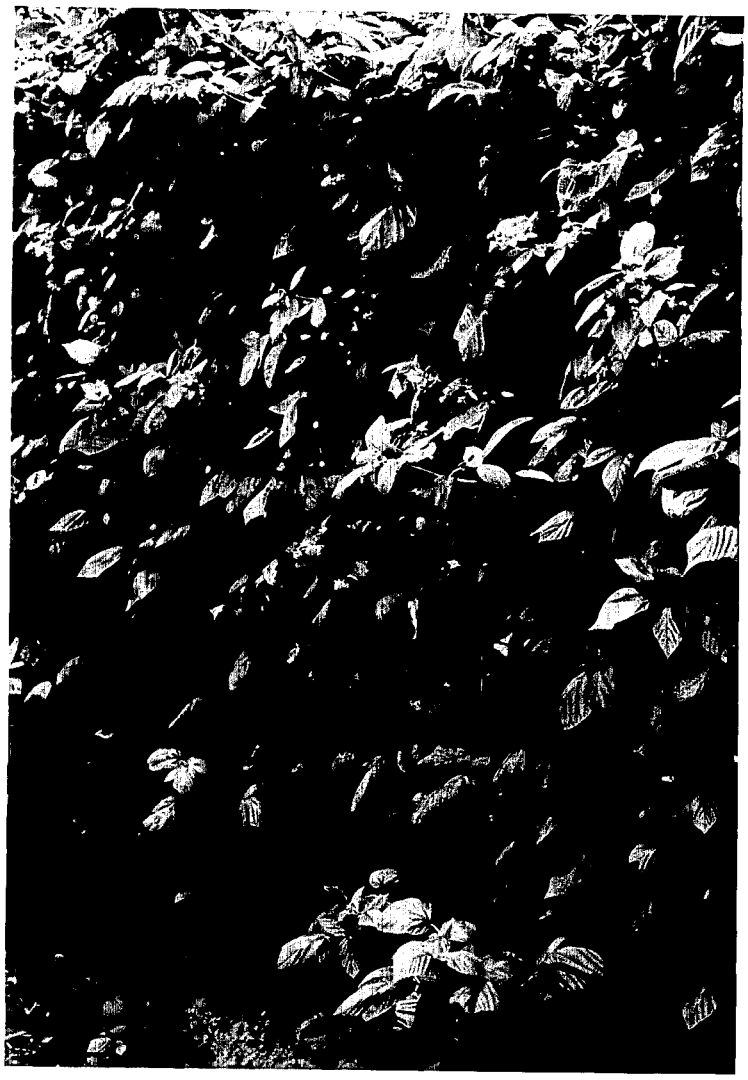

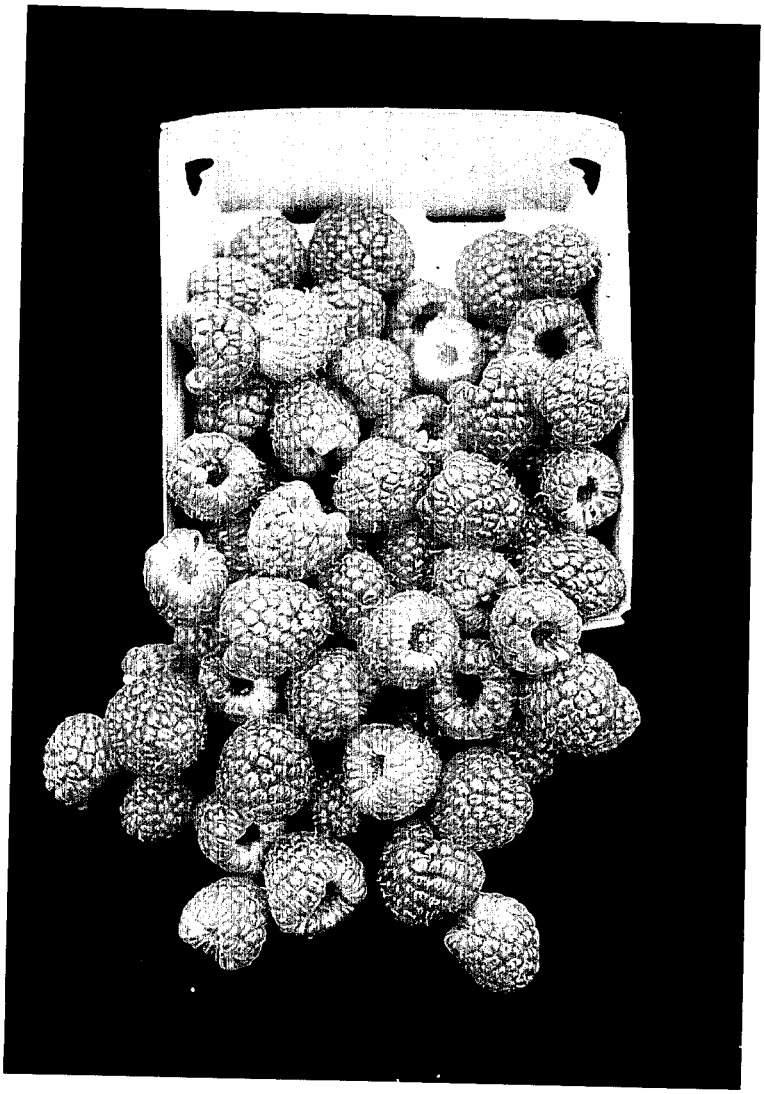

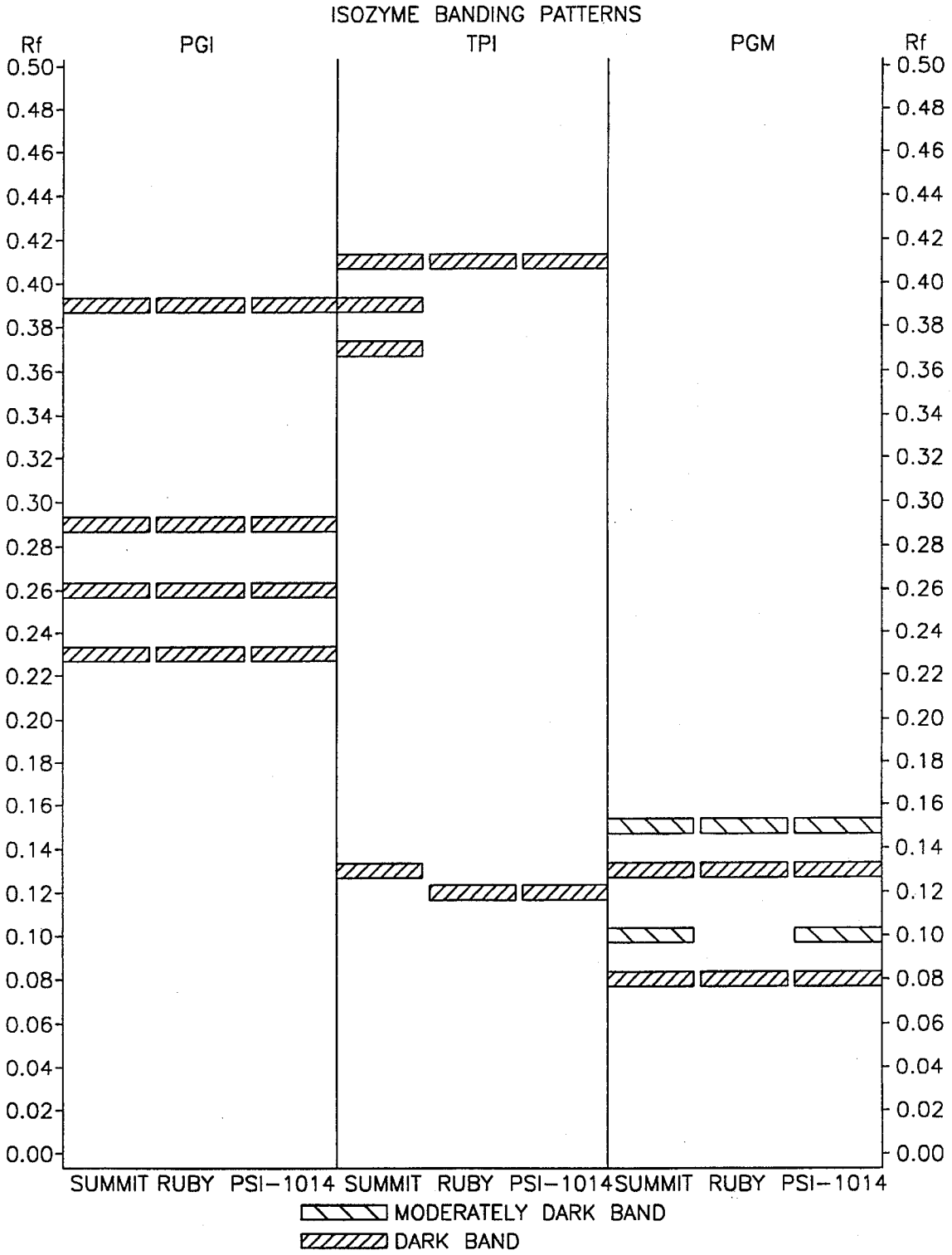
ISOZYME BANDING PATTERNS
Rf
PGI
TPI
PGM
Rf
0.50
0.48
0.46
0.44
0.42
0.40
0.38
0.36
0.34
0.32
0.30
0.28
0.26
0.24
0.22
0.20
0.18
0.16
0.14
0.12
0.10
0.08
0.06
0.04
0.02
0.00
SUMMIT RUBY PSI-1014 SUMMIT RUBY PSI-1014 SUMMIT RUBY PSI-1014
MODERATELY DARK BAND
DARK BAND